(12) United States Patent
Kitamura et al.

(10) Patent No.: US 9,012,761 B2
(45) Date of Patent: *Apr. 21, 2015

(54) ORGANIC PHOTOELECTRIC CONVERSION MATERIAL AND PHOTOELECTRIC CONVERSION ELEMENT USING THE SAME

(75) Inventors: Tetsu Kitamura, Ashigarakami-gun (JP); Kimiatsu Nomura, Ashigarakami-gun (JP); Tetsuro Mitsui, Ashigarakami-gun (JP)

(73) Assignee: FUJIFILM Corporation, Tokyo (JP)

(*) Notice: Subject to any disclaimer, the term of this patent is extended or adjusted under 35 U.S.C. 154(b) by 1146 days.

This patent is subject to a terminal disclaimer.

(21) Appl. No.: 12/401,962

(22) Filed: Mar. 11, 2009

(65) Prior Publication Data

US 2009/0229670 A1 Sep. 17, 2009

(30) Foreign Application Priority Data

Mar. 12, 2008 (JP) .................................. 2008-062955

(51) Int. Cl.
| | | |
|---|---|---|
| H02N 6/00 | (2006.01) | |
| H01L 31/042 | (2014.01) | |
| H01L 31/00 | (2006.01) | |
| C07D 213/57 | (2006.01) | |
| C07D 309/34 | (2006.01) | |
| C07D 335/02 | (2006.01) | |
| C07D 405/04 | (2006.01) | |
| C07D 413/10 | (2006.01) | |
| C07D 417/10 | (2006.01) | |
| H01L 51/00 | (2006.01) | |
| H01L 51/42 | (2006.01) | |

(52) U.S. Cl.
CPC ............ *C07D 213/57* (2013.01); *C07D 309/34* (2013.01); *C07D 335/02* (2013.01); *C07D 405/04* (2013.01); *C07D 413/10* (2013.01); *C07D 417/10* (2013.01); *H01L 51/0036* (2013.01); *H01L 51/0051* (2013.01); *H01L 51/0061* (2013.01); *H01L 51/0065* (2013.01); *H01L 51/4253* (2013.01); *Y02E 10/549* (2013.01)

(58) Field of Classification Search
CPC ..... H01L 51/0003; C08G 61/00; B82Y 10/00
USPC .................... 257/40; 136/263, 243, 244, 249; 549/426, 13; 546/330; 544/300, 41, 544/103
See application file for complete search history.

(56) References Cited

U.S. PATENT DOCUMENTS

| | | | |
|---|---|---|---|
| 4,145,215 A | * | 3/1979 | Van Allan et al. ............ 430/48 |
| 7,129,466 B2 | | 10/2006 | Iwasaki |
| 7,411,620 B2 | | 8/2008 | Taniguchi et al. |
| 2005/0217722 A1 | * | 10/2005 | Komatsu et al. ............ 136/263 |
| 2009/0085029 A1 | * | 4/2009 | Mitsui et al. ............... 257/40 |
| 2009/0189058 A1 | * | 7/2009 | Mitsui et al. ............... 250/208.1 |

FOREIGN PATENT DOCUMENTS

| | | | |
|---|---|---|---|
| JP | 2003-234460 A | | 8/2003 |
| JP | 2003-332551 A | | 11/2003 |
| JP | 2005032475 | * | 2/2005 |
| JP | 2005-197117 A | | 7/2005 |
| JP | 2005-203112 A | | 7/2005 |
| JP | 2005-268609 A | | 9/2005 |
| JP | 2007-227146 A | | 9/2007 |
| JP | 2007-227279 A | | 9/2007 |
| JP | 2009-088291 A | | 4/2009 |
| JP | 2009-200482 A | | 9/2009 |

OTHER PUBLICATIONS

Xuezhong Jiang, Sequestration of electroactive materials in a high Tg, insulating polymer matrix for optoelectronic applications. Part 2. Photovoltaic devices, 2006, Polymer, 47, 4124-4131.*
Jana Zaumseil et al. "Electron and Ambipolar Transport in Organic Field-Effect Transistors", Chem. Rev., 2007, 107(4), 1296-1323.
Serap Gnes et al. "Conjugated Polymer-Based Organic Solar Cells", Chem. Rev., 2007, 107(4), 1324-1338.
Chang He et al. "Synthesis and Photovoltaic Properties of a Solution-Processable Organic Molecule Containing Triphenylamine and DCM Moieties", J. Phys. Chem. C, 2007, 111(24)8661-8666.
Zhenan Bao et al., "Organic Field-Effect Transistors", 2007, published by CRC Press, pp. 159-228.
Office Action dated Oct. 9, 2012 in Japanese Application No. 2008-062955.

* cited by examiner

*Primary Examiner* — Monique Peets
(74) *Attorney, Agent, or Firm* — Sughrue Mion, PLLC

(57) ABSTRACT

An organic photoelectric conversion material for a photoelectric conversion element is provided, the organic photoelectric conversion material represented by formula 1 and having a molecular weight of 250 or greater but not greater than 800:

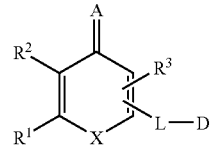

Formula 1 wherein, A represents an electron withdrawing atomic group; $R^1$, $R^2$ and $R^3$ each independently represents a hydrogen atom or a substituent; L represents a divalent π conjugated substituent; D represents an electron donating aromatic substituent; and X represents O, S, or N—$R^a$ in which $R^a$ represents a hydrogen atom or a substituent.

13 Claims, 1 Drawing Sheet

ORGANIC PHOTOELECTRIC CONVERSION MATERIAL AND PHOTOELECTRIC CONVERSION ELEMENT USING THE SAME

BACKGROUND OF THE INVENTION

1. Field of the Invention

The present invention relates to an organic photoelectric conversion material having a specific chemical structure and a high-performance organic thin-film photoelectric conversion element obtained using the photoelectric conversion material.

2. Description of the Related Art

Now, in a ubiquitous information society, information terminals which can be used any time anywhere are requested. There is therefore a demand for the development of flexible, light-weight, and inexpensive electronic devices, but conventional electronic devices using an inorganic semiconductor material such as silicon cannot sufficiently satisfy such a demand. Recently, much study has been made on electronic devices using an organic semiconductor material capable of meeting the demand (*Chemical Reviews*, 107, 1296-1323 (2007) and *Organic Field-Effect Transistors* (published in 2007 by CRC press), pp 159-228).

Organic thin-film photoelectric conversion elements are available by forming an organic semiconductor material into a thin film and using the thin film as a photoelectric conversion material. The organic thin-film photoelectric conversion element can take out, as energy, charges (carriers) generated by light so that it can be utilized as a solar cell (organic thin-film solar cell) (*Chemical Reviews*, 107, 1324-1338 (2007)) or can take them out as an electric signal so that it can be utilized as an optical sensor (solid-state pickup device) (Japanese Patent Laid-Open No. 2003-234460, Japanese Patent Laid-Open No. 2003-332551 and Japanese Patent Laid-Open No. 2005-268609).

Organic semiconductor materials are used advantageously as a photoelectric conversion material because use of them enables production of elements of a large area at a low cost in accordance with the process of application and also enables tuning of characteristics (for example, photoelectric conversion wavelength) of the elements by chemically modifying a photoelectric conversion material. Only limited substances such as phthalocyanines, fullerene derivatives, conductive polymers, and perylenetetracarboxylic acid derivatives offer a high performance as an organic photoelectric conversion material. They however are not easily imparted with solubility or cannot be chemically modified freely and thus, they cannot make full use of the advantage of the organic semiconductor materials. There is therefore a demand for the development of photoelectric conversion materials which can be formed into a film by the process of application, provide great possibility of chemical modification, and permit production of an organic thin-film photoelectric conversion element having a high performance.

Examples of the organic thin-film photoelectric conversion element exhibiting the best characteristics include elements having, as a photoelectric conversion film, a blend film of P3HT (poly(3-hexylthiophene)) and PCBM ([6,6]-Phenyl-C61-butyric acid methyl ester). This element shows a high photoelectric conversion performance, but is inferior in the performance to conventional silicon solar cells. There is therefore a demand for the development of elements exhibiting a higher photoelectric conversion performance (*Chemical Reviews*, 107, 1324-1338(2007)). Photoelectric conversion materials for organic photoelectric conversion elements having a molecular weight exceeding 800 are described in *J. Phys. Chem. C*, 111, 8661(2007), but these photoelectric conversion materials is low on photoelectric conversion performance.

SUMMARY OF THE INVENTION

The invention is made in consideration of the above-described background. An object of the invention is to provide an organic photoelectric conversion material which can be formed into a film by the process of application, can be subjected to various chemical modifications, and has a high photoelectric conversion performance; and a high-performance organic thin-film photoelectric conversion element using the organic photoelectric conversion material.

As a result of extensive investigation, the present inventors have found a photoelectric conversion material selected as described below and a high-performance organic thin-film photoelectric conversion material using the photoelectric conversion material.

That is, the present invention is as follows:

(1) An organic photoelectric conversion material represented by formula 1 and having a molecular weight of 250 or greater but not greater than 800:

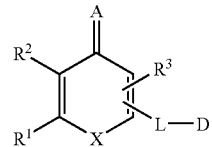

Formula 1 wherein, A represents an electron withdrawing atomic group;

$R^1$, $R^2$ and $R^3$ each independently represents a hydrogen atom or a substituent;

L represents a divalent π conjugated substituent;

D represents an electron donating aromatic substituent; and

X represents O, S, or N—$R^a$ in which $R^a$ represents a hydrogen atom or a substituent.

(2) The organic photoelectric conversion material according to item (1), which has a molecular weight of 300 or greater but not greater than 800.

(3) The organic photoelectric conversion material according to item (1), which has a molecular weight of 400 or greater but not greater than 800.

(4) The organic photoelectric conversion material according to (1), wherein the electron donating aromatic substituent represented by D in formula 1 contains an N,N-disubstituted aniline as a partial structure.

(5) The organic photoelectric conversion material according to item (4), which is represented by formula 2:

Formula 2

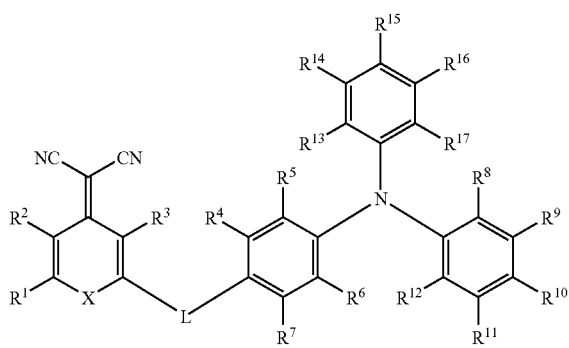

wherein, $R^1$ to $R^{17}$ each independently represents a hydrogen atom or a substituent;

L represents a divalent π conjugated substituent; and

X represents O, S, or N—$R^a$, in which $R^a$ represents a hydrogen atom or a substituent.

(6) A photoelectric conversion element, containing:
two electrode layers; and
a photoelectric conversion layer located between the two electrode layers,
wherein the photoelectric conversion layer contains the organic photoelectric conversion material according to any of items (1) to (5).

(7) The photoelectric conversion element according to item (6),
wherein the photoelectric conversion layer further contains an n-type organic semiconductor material.

(8) The photoelectric conversion element according to item (6),
wherein the photoelectric conversion layer contains a blend film containing the organic photoelectric conversion material according to any of items (1) to (5) and an n type organic semiconductor material.

(9) The photoelectric conversion element according to items (7) or (8),
wherein the n type organic semiconductor material is at least one selected from the group consisting of fullerene derivatives, phthalocyanines, naphthalenetetracarboxylic acid derivatives, and perylenetetracarboxylic acid derivatives.

(10) The photoelectric conversion element according to any of items (7) to (9),
wherein the n type organic semiconductor material is a fullerene derivative.

(11) The photoelectric conversion element according to any of items (6) to (10),
wherein the photoelectric conversion layer is formed by a solution application process.

(12) The photoelectric conversion element according to item (11),
wherein a solvent used in the solution application process includes at least one solvent having a boiling point of 135° C. or greater but less than 300° C.

(13) The photoelectric conversion element according to any of items (6) to (12), further containing a buffer layer having a conductive polymer, the buffer layer located between one of the two electrode layers and the photoelectric conversion layer.

(14) The photoelectric conversion element according to any of items (6) to (13), which is sealed in an inert atmosphere after formation of the photoelectric conversion element.

(15) The photoelectric conversion element according to any of items (6) to (14),
wherein the photoelectric conversion layer has a thickness of from 1 nm to 1 μm.

DETAILED DESCRIPTION OF THE INVENTION

Figure 1:
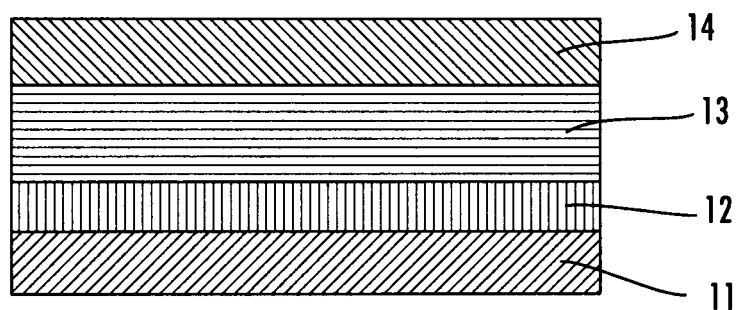
FIG. 1 is a cross-sectional view schematically illustrating the structure of the organic thin-film photoelectric conversion element of the invention.

The organic photoelectric conversion material to be used in the invention (which may hereinafter be called "organic photoelectric conversion material of the invention") has a molecular weight of preferably 250 or greater but not greater than 800, more preferably 300 or greater but not greater than 800, more preferably 400 or greater but not greater than 800. The molecular weight is preferably 250 or greater in order to obtain a thin film with good qualities. It is known that a purity of the organic semiconductor material has a large influence on the element performance, but an increase in molecular weight generally leads to reduction in solubility or reduction in sublimation properties, making it difficult to form a film or raise the purity. According to the investigation by the present inventors, when the molecular weight of the material represented by the below-described formula 1 is adjusted to 800 or less, the material can be purified by using, in combination, wet purification methods such as recrystallization and various column chromatographies and dry purification methods such as purification by sublimation and can have high purity. In particular, purification by sublimation is an effective method for purifying the organic semiconductor material and the material after purification by sublimation often becomes superior in element performance to that before purification. In addition, the photoelectric conversion material of the invention is also suited for film formation by vapor deposition because it has excellent sublimation properties.

The organic photoelectric conversion material to be used in the invention and represented by the formula 1 will next be described specifically.

Formula 1

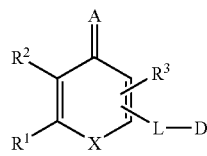

wherein, A represents an electron withdrawing atomic group, $R^1$ to $R^3$ each independently represents a hydrogen atom or a substituent, the substituent can be selected from the substituents W described later, and L represents a divalent π conjugated substituent, D represents an electron donating aromatic substituent, and X represents any one of O, S, or N—$R^a$, in which $R^a$ represents a hydrogen atom or a substituent.

The photoelectric conversion material of the formula 1 having a molecular weight of 250 or greater but not greater than 800 tends to cause charge separation because the electron withdrawing moiety and the electron donating moiety are linked via a π conjugated system. As a result, it becomes an excellent photoelectric conversion material having both an electron transport ability and a hole transport ability. The organic photoelectric conversion material can have desired performances (spectral sensitivity characteristics, amount of dark current, etc.) by selecting a proper structure for each moiety.

In the formula 1, A represents an electron withdrawing atomic group. The term "electron withdrawing atomic group" means an atomic group in which at least one electron withdrawing group has been bonded to an atom present at the binding site. Although no particular limitation is imposed on the electron withdrawing group, examples include substituents described in *Chem. Rev.*, 91, 165(1991) and having a positive Hammett constant. Specific examples include halogen atoms, a cyano group, a nitro group, perfluoroalkyl groups, and groups represented by —CO—R', —CO—CO—R', —SO—R', —SO$_2$—R', —C(=N—R")—R', —S(=NR")—R', —S(=NR")$_2$—R', —P(=O)R'$_2$, —O—R''', —S—R''', —N(—R")—CO—R', —N(—R")—SO—R', —N(—R")—SO$_2$—R', —N(—R")—C(=N—R")—R', —N(—R")—S(=NR")$_2$—R', and —N(—R")—P(=O)R'$_2$. In the above groups, R' represents a hydrogen atom, an alkyl group, an aryl group, a heterocyclic group, an amino group, an alkyloxy group, an aryloxy group, a heterocyclic oxy group, a hydroxy group, an alkylthio group, an arylthio group, a heterocyclic thio group, or a mercapto group. Specific examples are those shown later as examples of the substituents of W. R" represents a hydrogen atom, an alkyl group, an aryl group, a heterocyclic group, an acyl group, a sulfonyl group, a sulfinyl group, or a phosphoryl group. Specific examples are those shown later as examples of the substituents of W. R''' represents a perfluoroalkyl group, a cyano group, an acyl group, a sulfonyl group, or a sulfinyl group. Specific examples are those shown later as examples of the substituents of W. The group A has preferably from 1 to 30 carbon atoms, more preferably from 1 to 20 carbon atoms, still more preferably from 1 to 13 carbon atoms from the standpoint of a photoelectric conversion performance, solubility, and aptitude for purification by sublimation. Especially preferred specific examples of A will be described below, but the invention is not limited thereto. The mark * means a binding position.

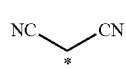

A-1

A-2

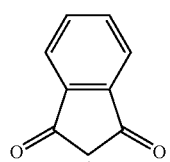

A-3

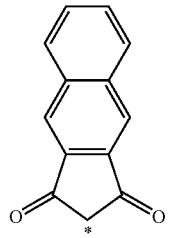

A-4

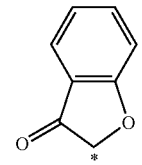

A-5

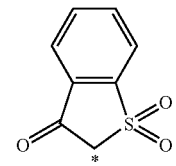

A-6

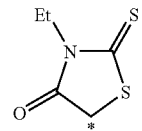

A-7

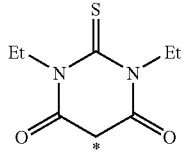

A-8

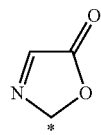

A-9

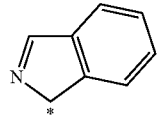

A-10

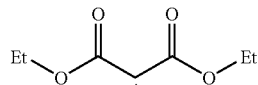

A-11

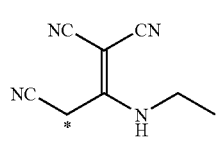

A-12

Of the above-described A-1 to A-12, A-1 and A-3 are especially preferred, with A-1 being most preferred.

In the formula 1, X represents any one of O, S, or N—R$^a$, more preferably O or S, even more preferably O. When X represents N—R$^a$, R$^a$ represents a hydrogen atom or a substituent and the substituent can be selected from the substituents W described later. From the standpoint of a photoelectric conversion performance, solubility, and aptitude for purification by sublimation, $R^a$ is a substituent having preferably from 1 to 20 carbon atoms, more preferably from 1 to 10 carbon atoms, still more preferably from 1 to 6 carbon atoms, even more preferably any one of alkyl groups, aryl groups and heterocyclic groups.

In the formula 1, D represents an electron donating aromatic substituent. The electron donating aromatic substituent is defined as an aromatic substituent having a higher electron density than that of an unsubstituted benzene ring, and causing oxidation easily but not causing reduction easily compared with the benzene. From the standpoint of a photoelectric conversion performance, solubility, and aptitude for purification by sublimation, the structure represented by D is a structure having preferably from 3 to 30 carbon atoms, more preferably from 6 to 20 carbon atoms. From the standpoint of the photoelectric conversion performance, the group represented by D contains, as a partial structure thereof, preferably N,N-disubstituted aniline, more preferably a triphenylamine structure. Particularly preferred specific examples will be shown below, but the invention is not limited thereto. The mark * represents a binding position.

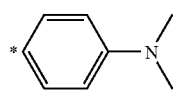

D-1

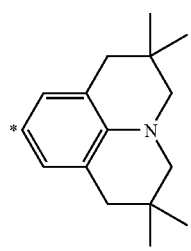

D-2

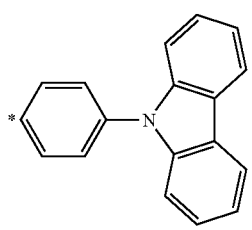

D-3

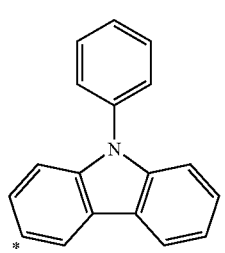

D-4

-continued

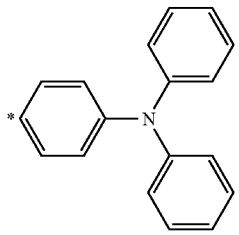

D-5

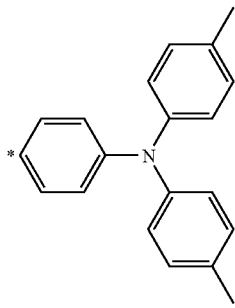

D-6

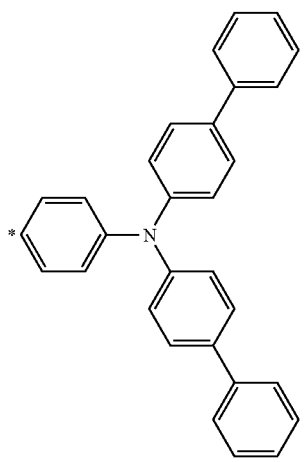

D-7

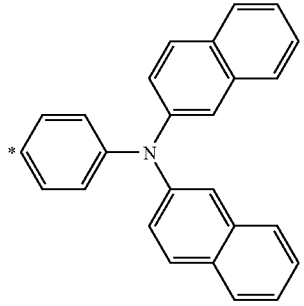

D-8

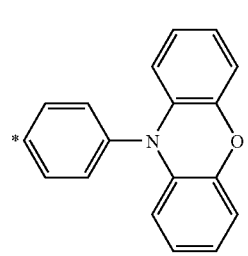

D-9

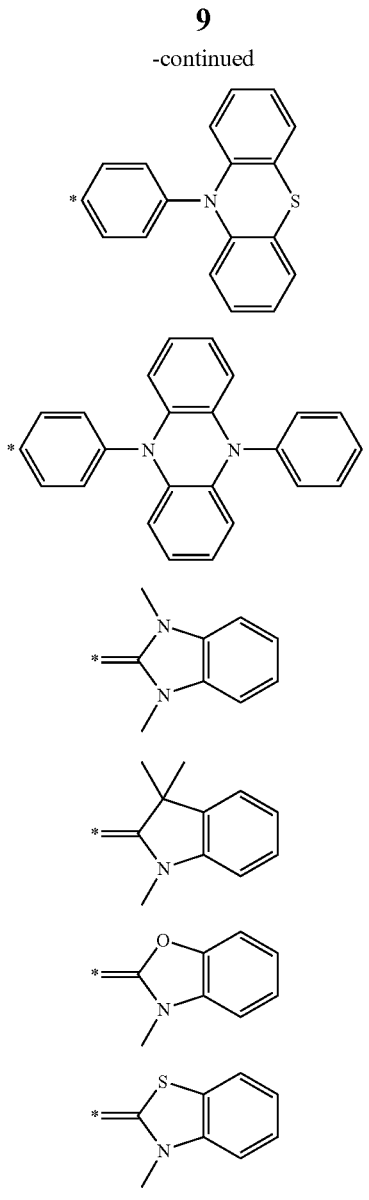

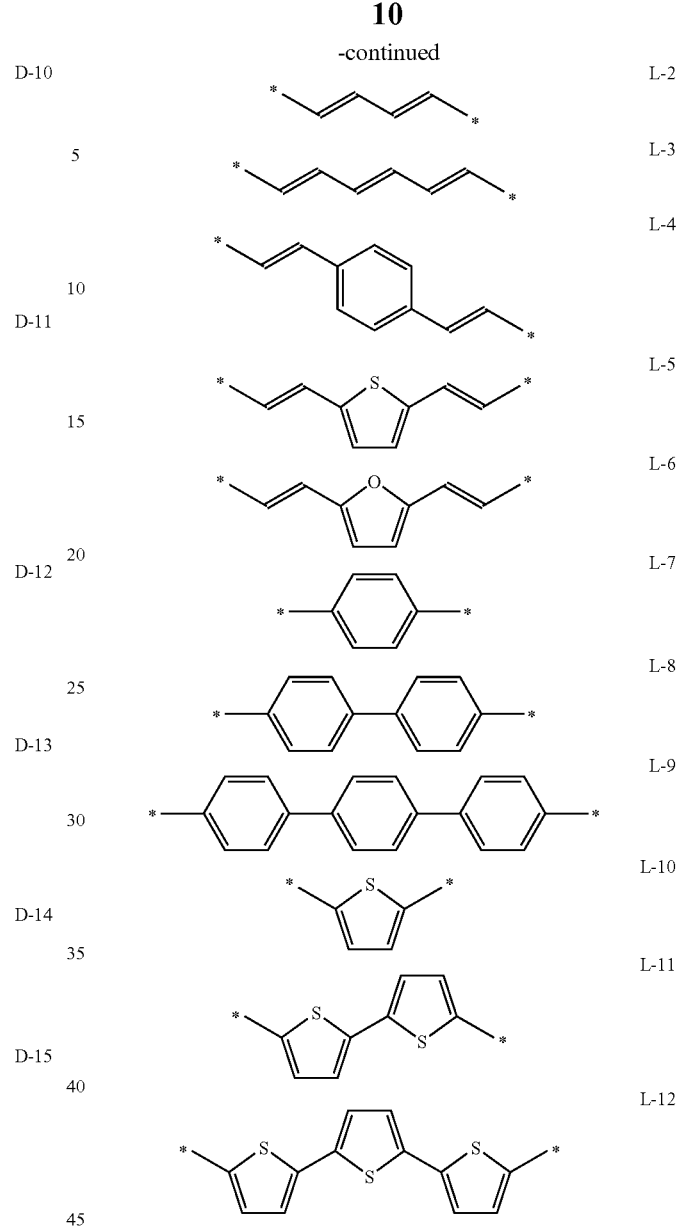

Of the D-1 to D-15, D-1, D-5, D-6, D-7, D-8, and D-15 are especially preferred, with D-5 and D-6 being most preferred.

In the formula 1, L represents a divalent π conjugated substituent. The term "divalent π conjugated substituent" as used herein means a substituent linked through a π conjugated system between two binding portions. Specific examples of it include substituents corresponding to those among the substituents W. From the standpoint of a photoelectric conversion performance, solubility, and aptitude for purification by sublimation, the divalent π conjugated substituents have preferably from 2 to 30 carbon atoms, more preferably from 2 to 20 carbon atoms, still more preferably from 2 to 12 carbon atoms. The following are preferred specific examples of L, but the invention is not limited thereto. The mark * means a binding position.

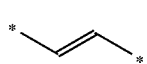

Of the above-described L-1 to L-12, L1-, L-2, L-3, and L-4 are especially preferred, with L-1 and L-2 being most preferred.

In the formula 1, $R^1$ to $R^3$ each independently represents a hydrogen atom or a substituent. The substituent can be selected from those given later as the substituent W. Use of these substituents enables to control the film formation property by the process of application, spectral sensitivity characteristics, resistance (amount of dark current) of the film, etc. $R^1$, $R^2$, and $R^3$ each represents preferably any of a hydrogen atom, a halogen atom, an alkyl group, an alkenyl group, an aryl group, a heterocyclic group, a cyano group, a nitro group, an alkoxy group, an aryloxy group, or a silyl group, more preferably any of a hydrogen atom, a halogen atom, an alkyl group, an alkenyl group, an aryl group, a heterocyclic group, an alkoxy group, an aryloxy group, or a silyl group, even more preferably any one of a hydrogen atom, an alkyl group, an alkenyl group, or an aryl group. It is also preferred that $R^1$ and $R^2$ may be coupled together to form a cyclic structure. It is also preferred that any of $R^1$ to $R^3$ has an L-D (L and D have the same meanings as those in the formula 1) structure. This means that the material having, in the molecule thereof, at least two L-D structures is also preferred because of having a high photoelectric conversion performance.

The organic photoelectric conversion material represented by the formula 1 has preferably a structure represented by the following formula 2:

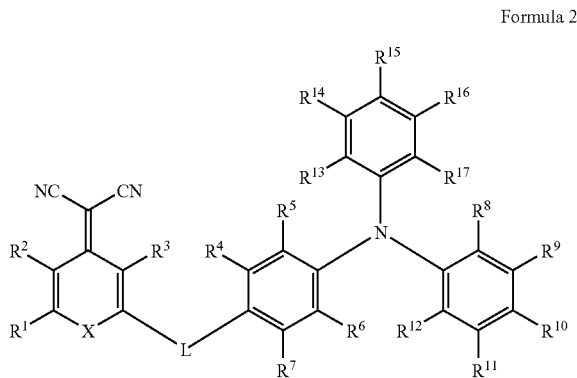

Formula 2

In the above formula, X and L have the same meaning as described above in the formula 1 and a preferable range of it is also the same.

In the above formula, $R^1$ to $R^3$ have the same meanings as described above in the formula 1 and a preferable range of them is also the same.

$R^4$ to $R^{17}$ each independently represents a hydrogen atom or a substituent. The substituent can be selected from the substituents W described later. $R^4$ to $R^{17}$ represents preferably any of a hydrogen atom, a halogen atom, an alkyl group, an aryl group, a heterocyclic group, a cyano group, a nitro group, an alkoxy group, an aryloxy group, or a silyl group, more preferably any of a hydrogen atom, a halogen atom, an alkoxy group, an aryl group, a heterocyclic group, an alkoxy group, an aryloxy group, or a silyl group, even more preferably any of a hydrogen atom, an alkyl group, an alkenyl group, or an aryl group. It is also preferred that two or more groups of $R^4$ to $R^{17}$ may be coupled together to form a cyclic structure. For example, $R^8$ and $R^9$, $R^9$ and $R^{10}$, $R^{13}$ and $R^{14}$, $R^{14}$ and $R^{15}$, and $R^5$ and $R^{13}$, $R^6$ and $R^{12}$, or $R^8$ and $R^{17}$ may be coupled together to form a ring.

In the invention, when a specific moiety of the substituent is called "a group", this means that the group itself may be unsubstituted or may be substituted further with one or more other substituents (up to a possible largest number). For example, the term "alkyl group" indicates a substituted or unsubstituted alkyl group. In short, the substituent of the compound may be substituted further in the invention.

When such a substituent is designated as W, the substituent represented by W may be any substituent and is not particularly limited, but examples thereof include halogen atoms, alkyl groups (including, as well as straight-chain or branched alkyl groups, cycloalkyl groups, bicycloalkyl groups, and tricycloalkyl groups), alkenyl groups (including, as well as straight-chain or branched alkenyl groups, cycloalkenyl group and bicycloalkenyl groups), alkynyl groups, aryl groups, heterocyclic groups, a cyano group, a hydroxyl group, a nitro group, a carboxyl group, alkoxy groups, aryloxy groups, silyloxy groups, heterocyclic oxy groups, acyloxy groups, carbamoyloxy groups, alkoxycarbonyloxy groups, aryloxycarbonyloxy groups, amino groups (including an anilino group), ammonio groups, acylamino groups, aminocarbonylamino groups, alkoxycarbonylamino groups, aryloxycarbonylamino groups, sulfamoylamino groups, alkyl- and aryl-sulfonylamino groups, a mercapto group, alkylthio groups, arylthio groups, heterocyclic thio groups, sulfamoyl groups, a sulfo group, alkyl- or aryl-sulfinyl groups, alkyl- or aryl-sulfonyl groups, acyl groups, aryloxycarbonyl groups, alkoxycarbonyl groups, carbamoyl groups, aryl- or heterocyclic azo groups, imide groups, phosphino groups, phosphinyl groups, phosphinyloxy groups, phosphinylamino groups, a phosphono group, silyl groups, hydrazino groups, ureido groups, a boronic acid group (—B(OH)$_2$), a phosphato group (—OPO(OH)$_2$), a sulfato group (—OSO$_3$H) and other known substituents.

More specifically, W represents any of the following atoms or groups (1) to (48).

(1) Halogen Atoms

They are, for example, fluorine, chlorine, bromine, iodine atoms.

(2) Alkyl Groups

They are straight-chain, branched or cyclic, substituted or unsubstituted alkyl groups and they also include the following groups (2-a) to (2-e):

(2-a) Alkyl Groups

They are preferably $C_{1-30}$ alkyl groups (such as methyl, ethyl, n-propyl, isopropyl, t-butyl, n-octyl, eicosyl, 2-chloroethyl, 2-cyanoethyl, and 2-ethylhexyl).

(2-b) Cycloalkyl Groups

They are preferably substituted or unsubstituted $C_{3-30}$ cycloalkyl groups (such as cyclohexyl, cyclopentyl, and 4-n-dodecylcyclohexyl).

(2-c) Bicycloalkyl Groups

They are preferably substituted or unsubstituted $C_{5-30}$ bicycloalkyl groups (such as bicyclo[1,2,2]heptan-2-yl and bicyclo[2,2,2]octan-3-yl).

(2-d) Tricycloalkyl Groups

They are preferably substituted or unsubstituted $C_{7-30}$ tricycloalkyl groups (such as 1-adamantyl).

(2-e) Polycyclic Cycloalkyl Groups Having Four or More Cyclic Structures

The alkyl group in the substituent described below (for example, an alkyl group in an alkylthio group) means an alkyl group based on such a concept. This will also apply to an alkenyl group and an alkynyl group.

(3) Alkenyl Groups

They are straight-chain, branched or cyclic, substituted or unsubstituted alkenyl groups and include the following alkenyl groups (3-a) to (3-c).

(3-a) Alkenyl Groups

They are preferably substituted or unsubstituted $C_{2-30}$ alkenyl groups (such as vinyl, allyl, prenyl, geranyl, and oleyl).

(3-b) Cycloalkenyl Groups

They are preferably substituted or unsubstituted $C_{3-30}$ cycloalkenyl groups (such as 2-cyclopenten-1-yl and 2-cyclohexen-1-yl).

(3-c) Bicycloalkenyl Groups

They are preferably substituted or unsubstituted bicycloalkenyl groups, preferably substituted or unsubstituted $C_{5-30}$ bicycloalkenyl groups (such as bicyclo[2,2,1]hept-2-en-1-yl and bicyclo[2,2,2]oct-2-en-4-yl)).

(4) Alkynyl Groups

They are preferably substituted or unsubstituted $C_2$-30 alkynyl groups (such as ethynyl, propargyl, and trimethylsilylethynyl).

(5) Aryl Groups

They are preferably substituted or unsubstituted $C_{6-30}$ aryl groups (such as phenyl, p-tolyl, naphthyl, m-chlorophenyl, o-hexadecanoylaminophenyl, and ferrocenyl).

(6) Heterocyclic Groups

They are preferably monovalent groups obtained by removing one hydrogen atom from 5- or 6-membered substituted or unsubstituted, aromatic or non-aromatic heterocyclic compounds, more preferably 5- or 6-membered aromatic $C_{2-50}$ heterocyclic groups (such as 2-furyl, 2-thienyl, 2-pyrimidinyl, and 2-benzothiazolyl and they may be a cationic heterocyclic group such as 1-methyl-2-pyridinio and 1-methyl-2-quinolinio).

(7) Cyano Group
(8) Hydroxyl Group
(9) Nitro Group
(10) Carboxyl Group
(11) Alkoxy Groups They are preferably substituted or unsubstituted $C_{1-30}$ alkoxy groups (such as methoxy, ethoxy, isopropoxy, t-butoxy, n-octyloxy, and 2-methoxyethoxy).

(12) Aryloxy Groups

They are preferably substituted or unsubstituted $C_{6-30}$ aryloxy groups (such as phenoxy, 2-methylphenoxy, 4-t-butylphenoxy, 3-nitrophenoxy, and 2-tetradecanoylaminophenoxy).

(13) Silyloxy Groups

They are preferably $C_{3-30}$ silyloxy groups (such as trimethylsilyloxy and t-butyldimethylsilyloxy).

(14) Heterocyclic Oxy Groups

They are preferably substituted or unsubstituted $C_{2-30}$ heterocyclic oxy groups (such as 1-phenyltetrazol-5-oxy and 2-tetrahydropyranyloxy).

(15) Acyloxy Groups

They are preferably a formyloxy group, substituted or unsubstituted $C_{2-30}$ alkylcarbonyloxy groups, and substituted or unsubstituted $C_{6-30}$ arylcarbonyloxy groups (such as formyloxy, acetyloxy, pivaloyloxy, stearoyloxy, benzoyloxy, and p-methoxyphenylcarbonyloxy).

(16) Carbamoyloxy Groups

They are preferably substituted or unsubstituted $C_{1-30}$ carbamoyloxy groups (such as N,N-dimethylcarbamoyloxy, N,N-diethylcarbamoyloxy, morpholinocarbonyloxy, N,N-di-n-octylaminocarbonyloxy, and N-n-octylcarbamoyloxy).

(17) Alkoxycarbonyloxy Groups

They are preferably substituted or unsubstituted $C_{2-30}$ alkoxycarbonyloxy groups (such as methoxycarbonyloxy, ethoxycarbonyloxy, t-butoxycarbonyloxy, and n-octylcarbonyloxy).

(18) Aryloxycarbonyloxy Groups

They are preferably substituted or unsubstituted $C_{7-30}$ aryloxycarbonyloxy groups (such as phenoxycarbonyloxy, p-methoxyphenoxycarbonyloxy, and p-n-hexadecyloxyphenoxycarbonyloxy).

(19) Amino Groups

They are preferably an amino group, substituted or unsubstituted $C_{1-30}$ alkylamino groups, or substituted or unsubstituted $C_{6-30}$ anilino groups (such as amino, methylamino, dimethylamino, anilino, N-methyl-anilino, and diphenylamino).

(20) Ammonio Groups

They are preferably an ammonio group or ammonio groups substituted with a substituted or unsubstituted $C_{1-30}$ alkyl, aryl or heterocycle (such as trimethylammonio, triethylammonio, and diphenylmethylammonio).

(21) Acylamino Groups

They are preferably a formylamino group, substituted or unsubstituted $C_{1-30}$ alkylcarbonylamino groups, or substituted or unsubstituted $C_{6-30}$ arylcarbonylamino groups (such as formylamino, acetylamino, pivaloylamino, lauroylamino, benzoylamino, and 3,4,5-tri-n-octyloxyphenylcarbonylamino).

(22) Aminocarbonylamino Groups

They are preferably substituted or unsubstituted $C_{1-30}$ aminocarbonylamino groups (such as carbamoylamino, N,N-dimethylaminocarbonylamino, N,N-diethylaminocarbonylamino, and morpholinocarbonylamino).

(23) Alkoxycarbonylamino Groups

They are preferably substituted or unsubstituted $C_{2-30}$ alkoxycarbonylamino groups (such as methoxycarbonylamino, ethoxycarbonylamino, t-butoxycarbonylamino, n-octadecyloxycarbonylamino, and N-methyl-methoxycarbonylamino).

(24) Aryloxycarbonylamino Groups

They are preferably substituted or unsubstituted $C_{7-30}$ aryloxycarbonylamino groups (such as phenoxycarbonylamino, p-chlorophenoxycarbonylamino, and m-n-octyloxyphenoxycarbonylamino).

(25) Sulfamoylamino Groups

They are preferably substituted or unsubstituted $C_{0-30}$ sulfamoylamino groups (such as sulfamoylamino, N,N-dimethylaminosulfonylamino, and N-n-octylaminosulfonylamino).

(26) Alkyl- or Arylsulfonylamino Groups

They are preferably substituted or unsubstituted $C_{1-30}$ alkylsulfonylamino groups and substituted or unsubstituted $C_{6-30}$ arylsulfonylamino groups (such as methylsulfonylamino, butylsulfonylamino, phenylsulfonylamino, 2,3,5-trichlorophenylsulfonylamino, and p-methylphenylsulfonylamino).

(27) Mercapto Group
(28) Alkylthio Groups

They are preferably substituted or unsubstituted $C_{1-30}$ alkylthio groups (such as methylthio, ethylthio, and n-hexadecylthio).

(29) Arylthio Groups

They are preferably substituted or unsubstituted $C_{6-30}$ arylthio groups (such as phenylthio, p-chlorophenylthio, and m-methoxyphenylthio).

(30) Heterocyclic Thio Groups

They are preferably substituted or unsubstituted $C_{2-30}$ heterocyclic thio groups (such as 2-benzothiazolylthio and 1-phenyltetrazol-5-ylthio).

(31) Sulfamoyl Groups

They are preferably substituted or unsubstituted $C_{0-30}$ sulfamoyl groups (such an N-ethylsulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl)sulfamoyl)).

(32) Sulfo Group
(33) Alkyl- or Aryl-Sulfinyl Groups

They are preferably substituted or unsubstituted $C_{1-30}$ alkylsulfinyl groups and substituted or unsubstituted $C_{6-30}$ arylsulfinyl groups (such as methylsulfinyl, ethylsulfinyl, phenylsulfinyl, and p-methylphenylsulfinyl).

(34) Alkyl- or Aryl-Sulfonyl Groups

They are preferably substituted or unsubstituted $C_{1-30}$ alkylsulfonyl groups and substituted or unsubstituted $C_{7-30}$ arylsulfonyl groups (such as methylsulfonyl, ethylsulfonyl, phenylsulfonyl, and p-methylphenylsulfonyl).

(35) Acyl Groups

They are preferably a formyl group, substituted or unsubstituted $C_{2-30}$ alkylcarbonyl groups, substituted or unsubstituted $C_{7-30}$ arylcarbonyl groups, and substituted or unsubstituted $C_{4-30}$ heterocyclic carbonyl groups bonded to the carbonyl group via the carbon atom (such as acetyl, pivaloyl, 2-chloroacetyl, stearoyl, benzoyl, p-n-octyloxyphenylcarbonyl, 2-pyridylcarbonyl, and 2-furylcarbonyl).

(36) Aryloxycarbonyl Groups

They are preferably substituted or unsubstituted $C_{7-30}$ aryloxycarbonyl groups (such as phenoxycarbonyl, o-chlorophenoxycarbonyl, m-nitrophenoxycarbonyl, and p-t-butylphenoxycarbonyl).

(37) Alkoxycarbonyl Groups

They are preferably substituted or unsubstituted $C_{2-30}$ alkoxycarbonyl groups (such as methoxycarbonyl, ethoxycarbonyl, t-butoxycarbonyl, and n-octadecyloxycarbonyl).

(38) Carbamoyl Groups

They are preferably substituted or unsubstituted $C_{1-30}$ carbamoyl groups (such as carbamoyl, N-methylcarbamoyl, N,N-dimethylcarbamoyl, N,N-di-n-octylcarbamoyl, and N-(methylsulfonyl)carbamoyl)).

(39) Aryl or Heterocyclic Azo Groups

They are preferably substituted or unsubstituted $C_{6-30}$ arylazo groups and substituted or unsubstituted $C_{2-30}$ heterocyclic azo groups (such as phenylazo, p-chlorophenylazo, and 5-ethylthio-1,3,4-thiadiazol-2-ylazo).

(40) Imide Groups

They are preferably N-succinimide and N-phthalimide.

(41) Phosphino Groups

They are preferably substituted or unsubstituted $C_{2-30}$ phosphino groups (such as dimethylphosphino, diphenylphosphino, and methylphenoxyphosphino).

(42) Phosphinyl Groups

They are preferably substituted or unsubstituted $C_{2-30}$ phosphinyl groups (such as phosphinyl, dioctyloxyphosphinyl, and diethoxyphosphinyl).

(43) Phosphinyloxy Groups

They are preferably substituted or unsubstituted $C_{2-30}$ phosphinyloxy groups (such as diphenoxyphosphinyloxy and dioctyloxyphosphinyloxy).

(44) Phosphinylamino Groups

They are preferably substituted or unsubstituted $C_{2-30}$ phosphinylamino groups (such as dimethoxyphosphinylamino and dimethylaminophosphinylamino).

(45) Phospho Group

(46) Silyl Groups

They are preferably substituted or unsubstituted $C_{3-30}$ silyl groups (such as trimethylsilyl, triethylsilyl, triisopropylsilyl, t-butyldimethylsilyl and phenyldimethylsilyl).

(47) Hydrazino Groups

They are preferably substituted or unsubstituted $C_{0-30}$ hydrazino groups (such as trimethylhydrazino).

(48) Ureido Groups

They are preferably substituted or unsubstituted $C_{0-30}$ ureido groups (such as N,N-dimethylureido).

Also, two Ws may be coupled together to form a ring. Such a ring is, for example, an aromatic or non-aromatic hydrocarbon ring or a heterocycle, or a polycyclic condensed ring comprising a plurality of these rings. Examples thereof include a benzene ring, a naphthalene ring, an anthracene ring, a phenanthrene ring, a fluorene ring, a triphenylene ring, a naphthacene ring, a biphenyl ring, a pyrrole ring, a furan ring, a thiophene ring, an imidazole ring, an oxazole ring, a thiazole ring, a pyridine ring, a pyrazine ring, a pyrimidine ring, a pyridazine ring, an indolizine ring, an indole ring, a benzofuran ring, a benzothiophene ring, an isobenzofuran ring, a quinolizine ring, a quinoline ring, a phthalazine ring, a naphthyridine ring, a quinoxaline ring, a quinoxazoline ring, an isoquinoline ring, a carbazole ring, a phenanthridine ring, an acridine ring, a phenanthroline ring, a thianthrene ring, a chromene ring, a xanthene ring, a phenoxathiin ring, a phenothiazine ring, and a phenazine ring. Of these, a benzene ring, a pyrrole ring, a furan ring, a thiophene ring, an imidazole ring, an oxazole ring, a thiazole ring, a pyridine ring, and a pyrazine ring are preferable cyclic compounds.

Of these substituents W, those having a hydrogen atom may be deprived of the hydrogen atom and substituted further with the above-described substituent. Examples of such a substituent include a —CONHSO$_2$— group (such as sulfonylcarbamoyl group or carbonylsulfamoyl group), a —CONHCO— group (such as carbonylcarbamoyl group) and an —SO$_2$NHSO$_2$— group (such as sulfonylsulfamoyl group). Specific examples thereof include alkylcarbonylaminosulfonyl groups (such as acetylaminosulfonyl), arylcarbonylaminosulfonyl groups (such as benzoylaminosulfonyl), alkylsulfonylaminocarbonyl groups (such as methylsulfonylaminocarbonyl), and arylsulfonylaminocarbonyl groups (such as p-methylphenylsulfonylaminocarbonyl).

The following are preferred specific examples of the photoelectric conversion material of the invention represented by the formula 1 or the formula 2, but the invention is not limited to the following examples.

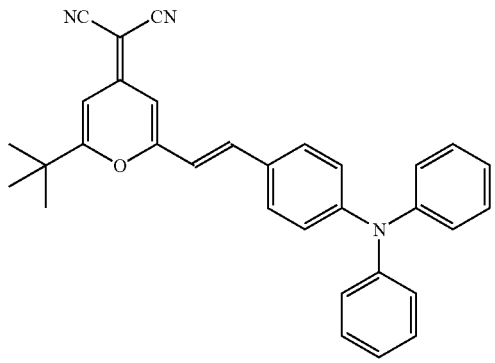

Compound 1

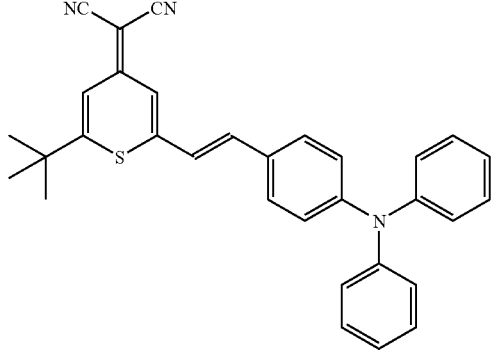

Compound 2

Compound 3
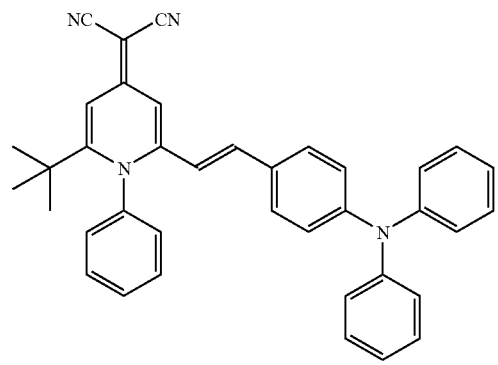
Compound 4
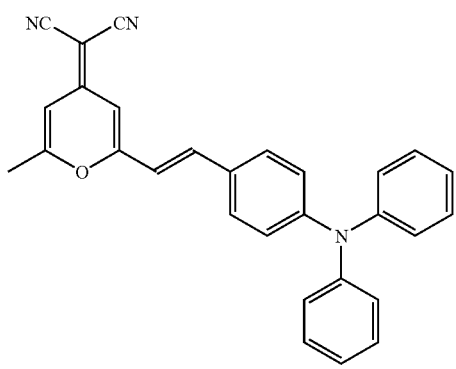
Compound 5
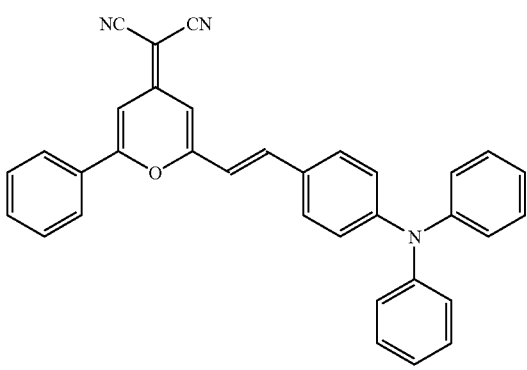
Compound 6
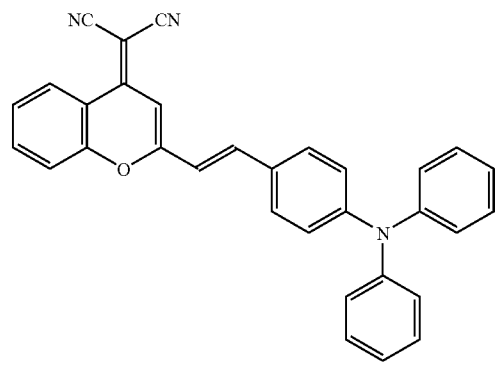
Compound 7
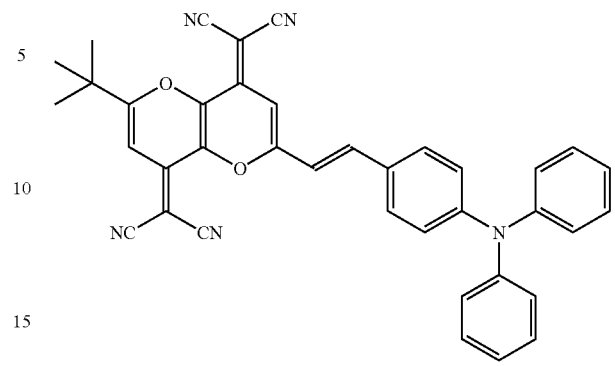
Compound 8
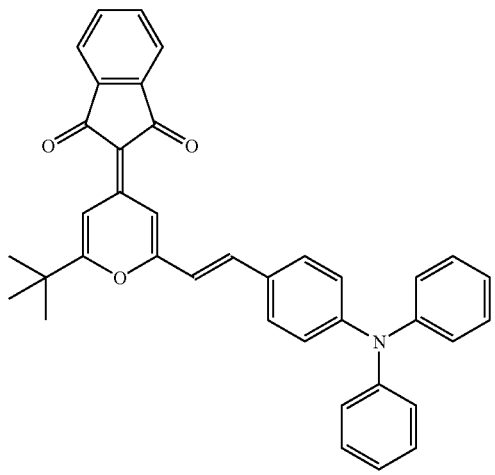
Compound 9
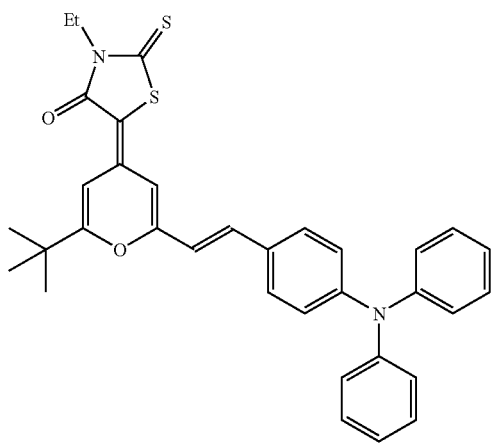

Compound 10
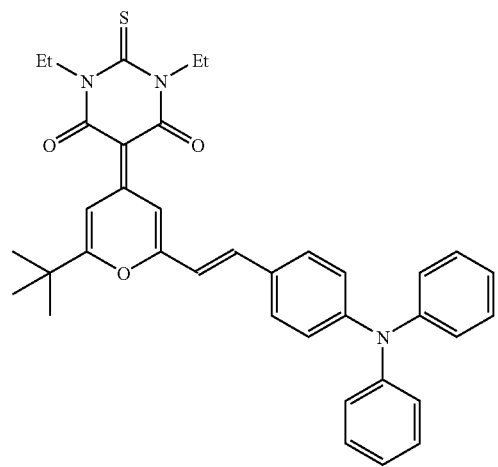
Compound 11
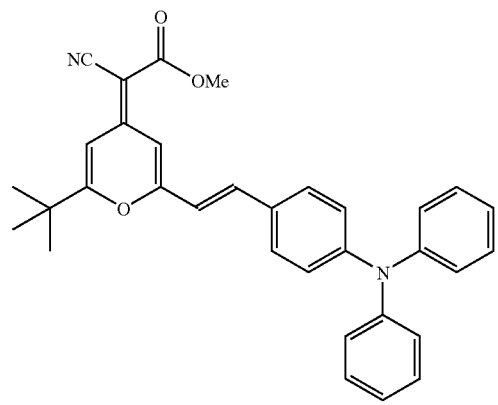
Compound 12
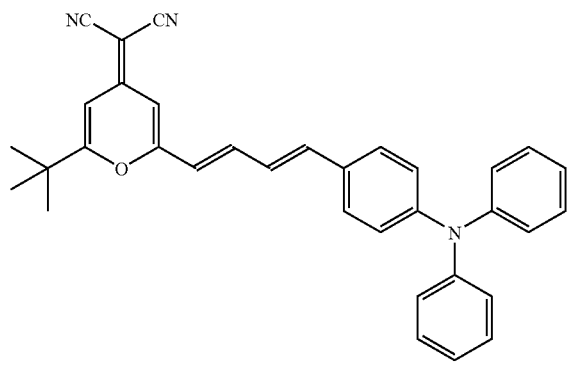
Compound 13
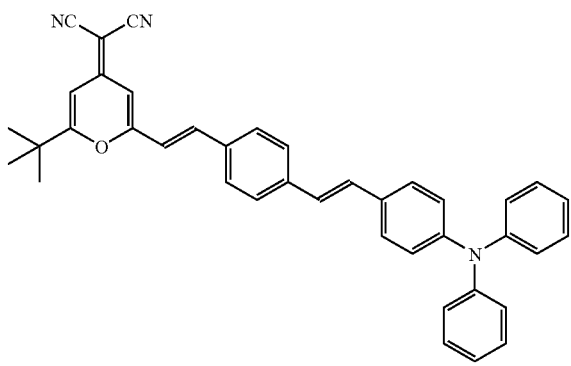
Compound 14
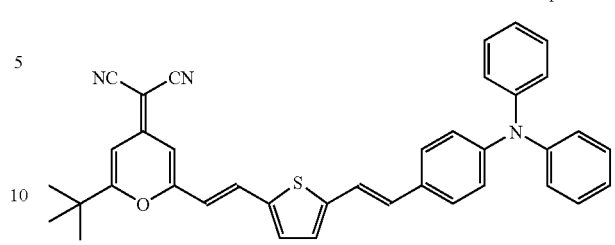
Compound 15
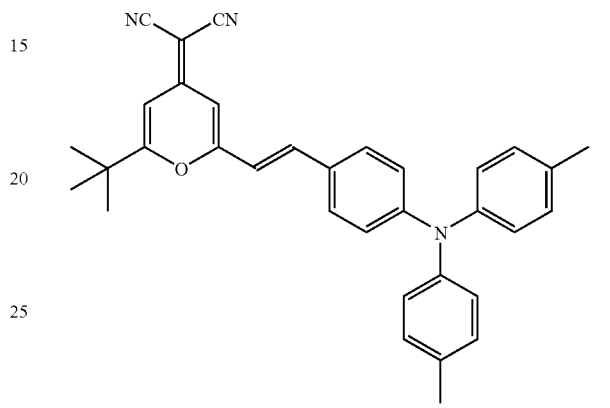
Compound 16
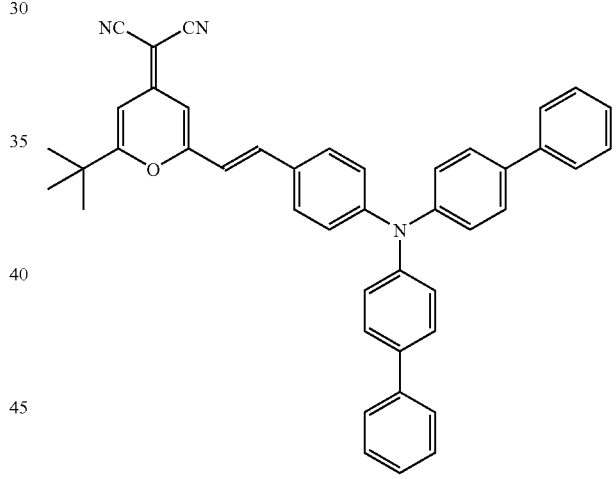
Compound 17
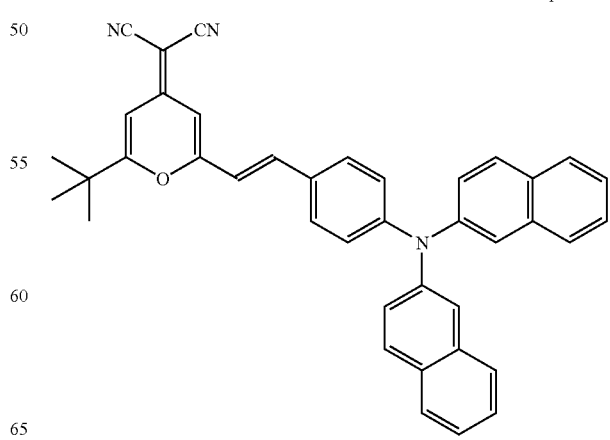

Compound 18
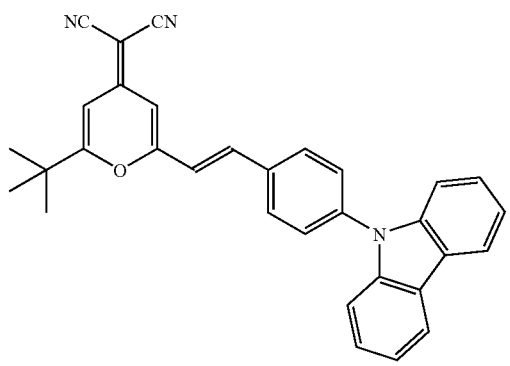
Compound 19
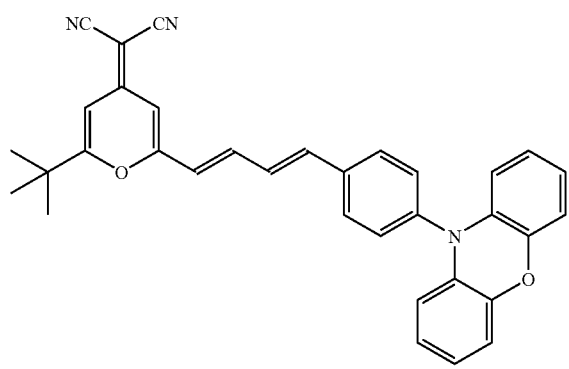
Compound 20
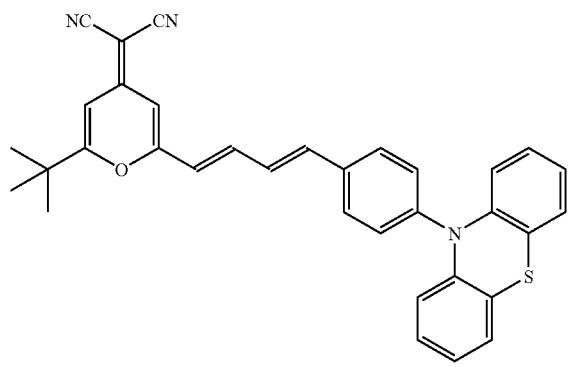
Compound 21
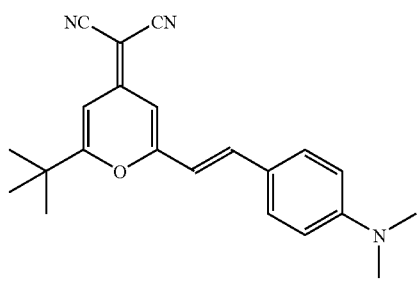
Compound 22
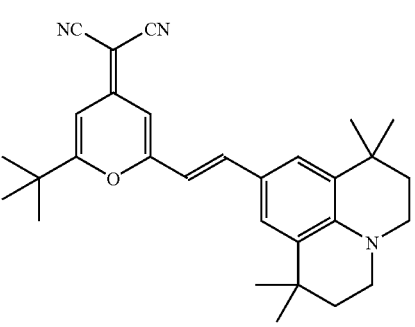
Compound 23
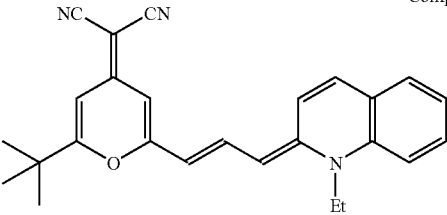
Compound 24
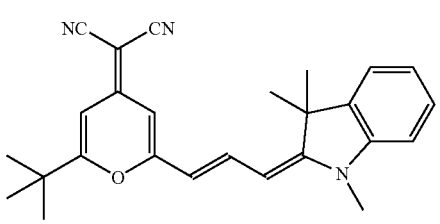
Compound 25
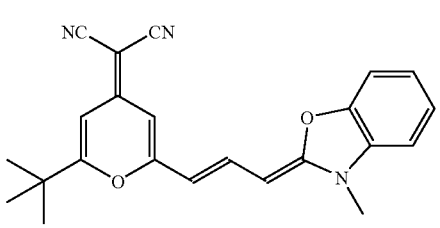
Compound 26
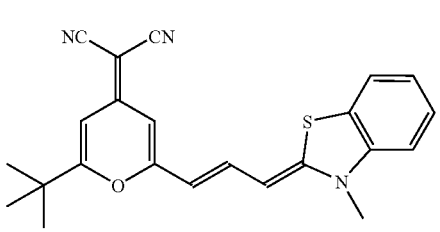
Compound 27
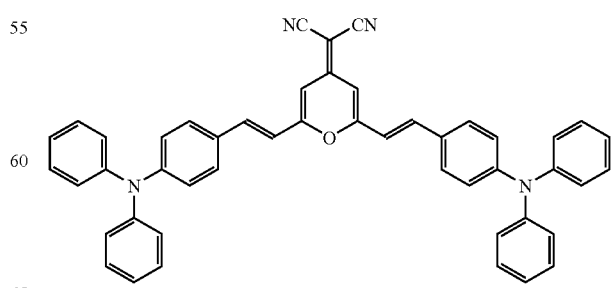

Compound 28

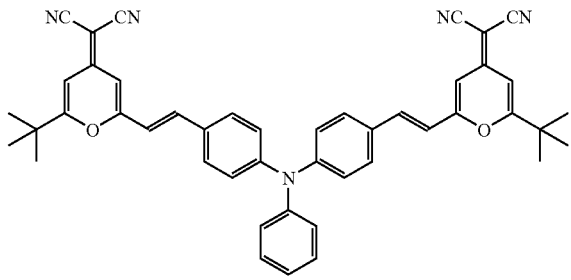

The organic photoelectric conversion material of the invention will be described in more specifically.

The term "organic semiconductor material" as used herein means an organic material having properties of a semiconductor. In the invention, it may be, in other words, an organic material having an ability of transporting carriers (holes or electrons). Similar to semiconductors made of an inorganic material, there are p type organic semiconductor materials transporting holes as carriers (which may also be called "hole transport materials") and n type organic semiconductor materials transporting electrons as carriers (which may also be called "electron transport materials). The term "organic photoelectric conversion material" means a material having a carrier transport performance and at the same time, having an ability of generating carriers by exposure to light. They are one of organic semiconductor materials.

The organic photoelectric conversion materials of the invention can be easily formed into a thin film with good qualities so that they are suited for preparation of a thin film. In forming a thin film, the film may be a mixture of the organic photoelectric conversion material with a binder material and another organic semiconductor material. In this case, the content of the compound of the invention in the film is preferably 1 mass % or greater, more preferably 5 mass % or greater, still more preferably 10 mass % or greater. Although no particular limitation is imposed on the thickness of the photoelectric conversion layer, it is preferably from 1 nm to 1 μm, more preferably 5 nm to 500 nm.

Although the thin film containing the organic photoelectric conversion material of the invention may be formed by any process, it is formed by a dry process or a wet process, with the wet process being preferred. Specific examples of the dry process include physical vapor deposition such as vacuum vapor deposition, sputtering, ion plating, and molecular beam epitaxy (MBE), and chemical vapor deposition (CVD) such as plasma polymerization. In the wet process film formation, the organic photoelectric conversion material is dissolved in a solvent capable of dissolving the material therein or dispersed uniformly in the solvent and a film is formed using the solution or dispersion (solution application process). Specific examples include casting, blade coating, wire bar coating, spray coating, dipping coating, bead coating, air knife coating, curtain coating, inkjet printing, spin coating, and Langmuir-Blodgett (LB). Of these, casting, spin coating, and inkjet printing are preferred, with spin coating being more preferred.

When a thin film of organic photoelectric coversion material used for a photoelectric coversion layer is formed by the wet process, the organic photoelectric conversion material or the material for the organic photoelectric conversion material and a binder resin are dissolved or dispersed in an appropriate organic solvent (a hydrocarbon solvent such as hexane, octane, decane, toluene, xylene, ethylbenzene, 1-methylnaphthalene, or 1,2-dichlorobenzene, a ketone solvent such as acetone, methyl ethyl ketone, methyl isobutyl ketone, or cyclohexanone, a halogenated hydrocarbon solvent such as dichloromethane, chloroform, tetrachloromethane, dichloroethane, trichloroethane, tetrachloroethane, chlorobenzene, dichlorobenzene, or chlorotoluene, an ester solvent such as ethyl acetate, butyl acetate, or amyl acetate, an alcohol solvent such as methanol, propanol, butanol, pentanol, hexanol, cyclohexanol, methyl cellosolve, ethyl cellosolve, or ethylene glycol, an ether solvent such as dibutyl ether, tetrahydrofuran, dioxane, or anisole, or a polar solvent such as N,N-dimethylformamide, N,N-dimethylacetamide, 1-methyl-2-pyrrolidone, 1-methyl-2-imidazolidinone, or dimethyl sulfoxide) and/or water to prepare a coating solution, and a thin film can be formed by various processes of application. Any solvent is usable but a solvent mixture containing a solvent having a high boiling point is preferred because the solvent having a high boiling point retards the evaporation speed and improves an arrangement order of molecules in the film thus formed. The solvent mixture contains a solvent having a boiling point of 135° C. or greater but less than 300° C. (more preferably 135° C. or greater but less than 210° C.) preferably in an amount of 1 mass % or greater but not greater than 100 mass % based on the total mass of the solvents. Examples of such a solvent include ethyl cellosolve (boiling point: 135° C.), n-amyl alcohol (boiling point: 137° C.), xylene (boiling point: 140° C.), amyl acetate (boiling point: 142° C.), β-picoline (boiling point: 143° C.), 1,1,2,2-tetrachloroethane (boiling point: 146° C.), N,N-dimethylformamide (boiling point: 153° C.), 1-hexanole (boiling point: 157° C.), o-chlorotoluene (boiling point: 159° C.), pentachloroethane (boiling point: 162° C.), N,N-dimethylacetamide (boiling point: 165° C.), o-dichlorobenzene (boiling point: 180° C.), dimethylsulfoxide (boiling point: 189° C.), ethylene glycol (boiling point: 198° C.), 1-methyl-2-pyrrolidone (boiling point: 202° C.), nitrobenzene (boiling point: 211° C.), 1,2,4-trichlorobenzene (boiling point: 214° C.), quinoline (boiling point: 238° C.), and 1-chloronaphthalene (boiling point: 260° C.). Of these, xylene, β-picoline, o-chlorotoluene, and o-dichlorobenzene are particularly preferred. A film with a desired thickness can be formed by adjusting the concentration of the photoelectric conversion material of the invention in the coating solution to preferably from 0.1 to 80 mass %, more preferably from 0.1 to 30 mass %, still more preferably from 0.1 to 10 mass %.

When a resin binder is used, examples of the resin binder include insulating polymers such as polystyrene, polycarbonate, polyarylate, polyester, polyamide, polyimide, polyurethane, polysiloxane, polysulfone, poly(methyl methacrylate), poly(methyl acrylate), cellulose, polyethylene, and polypropylene, and copolymers thereof, photoconductive polymers such as polyvinyl carbazole and polysilane, and conductive polymers such as polythiophene, polypyrrole, polyaniline, and polyparaphenylene vinylene. These resin binders may be used eithers ingly or in combination. In consideration of the mechanical strength of the resulting film, resin binders having a high glass transition point are preferred. In consideration of a charge transfer degree, resin binders, photoconductive polymers or conductive polymers free from a polar group are preferred. Although the resin binder is preferably omitted in consideration of its properties, it may be used according to the intended use. When it is used, an amount of the resin binder is not particularly limited but is preferably from 0.1 to 90 mass %, more preferably from 0.1 to 50 mass %, still more preferably from 0.1 to 30 mass % in the organic photoelectric conversion layer.

Upon film formation, a substrate may be heated or cooled. Morphology or molecular orientation state of the film can be controlled by changing the temperature of the substrate. Although no particular limitation is imposed on the temperature of the substrate, it is preferably between 0° C. to 200° C.

The constitution of the photoelectric conversion element of the invention will hereinafter be described in detail.

FIG. 1 is a cross-sectional view schematically illustrating the structure of the organic thin-film photoelectric conversion element of the invention. The element of FIG. 1 has a stacked structure. It has, as the bottom layer thereof, a substrate 11 and an electrode layer 12 is disposed over the upper surface of the substrate. As the upper layer of the electrode layer, a photoelectric conversion layer 13 containing the photoelectric conversion material of the invention is placed. An electrode layer 14 is laid over the upper surface of the photoelectric conversion layer. A buffer layer for enhancing flatness and smoothness of the surface, a carrier injection layer for accelerating injection of holes or electrons from an electrode, a carrier transport layer for transporting holes or electrons, or a carrier block layer for blocking holes or electrons (one layer may have two or more functions) may be placed between the electrode layer 12 or 14 and the photoelectric conversion layer 13. In the invention, these layers placed between the electrode layer and the photoelectric conversion layer will hereinafter be called "buffer layer" irrespective of their role. The electrode layer or each layer does not necessarily have a flat surface and it may have a deeply indented surface or a three-dimensional (for example, comb-like) shape.

No particular limitation is imposed on the material of the substrate 11 insofar as it transmits visible light or infrared light. The material has preferably a visible-light or infrared-light transmittance of 60% or greater, more preferably 80% or greater, even more preferably 90% or greater. Examples of such a material include polyester films such as polyethylene naphthoate (PEN) and polyethylene terephthalate (PET), polyimide film, ceramic, silicon, quartz, and glass. The thickness of the substrate is not particularly limited.

The material used as the electrode layer 12 is not particularly limited insofar as it transmits visible light or infrared light and exhibits conductivity. The visible light transmittance or infrared light transmittance is preferably 60% or greater, more preferably 80% or greater, even more preferably 90% or greater. Examples of such a material include transparent conductive oxides such as ITO, IZO, $SnO_2$, ATO (antimony-doped tin oxide), ZnO, AZO (Al-doped zinc oxide), GZO (gallium-doped zinc oxide), $TiO_2$, and FTO (fluorine-doped tin oxide). Of these, ITO and IZO are particularly preferred from the standpoint of processing aptitude, flatness and smoothness. The film thickness is not particularly limited, but it is preferably from 1 nm to 200 nm, more preferably from 5 nm to 100 nm. When the electrode 12 has self-sustainability, the substrate 11 is not always necessary. When the electrode 12 serves as the substrate 11, the thickness may be greater than the above-described range.

The photoelectric conversion layer 13 contains the photoelectric conversion material of the invention. It may be a single layer composed of the photoelectric conversion material of the invention or may have a stacked structure thereof with a layer containing another semiconductor material (in this case, the stacking order or the number of layers to be stacked is not limited). Alternatively, it may be a layer containing both the photoelectric conversion material of the invention and another semiconductor material (in this case, they are mixed completely at a molecular level or may form a certain phase-separated structure). As the another semiconductor material, n-type semiconductor materials are preferred and use of, as the photoelectric conversion layer, a layer containing a blend film of the photoelectric conversion material of the invention and the n type semiconductor material is most preferred.

As the n type semiconductor material to be used in the invention, any of organic semiconductor materials and inorganic semiconductor materials are usable insofar as it has an electron transport property. Preferred examples include fullerene derivatives, phthalocyanines, naphthalenetetracarboxylic acid derivatives, perylenetetracarboxylic acid derivatives and inorganic semiconductors, of which ftillerene derivatives, phthalocyanines, naphthalenetetracarboxylic acid derivatives, and perylenetetracarboxylic acid derivatives are more preferred and fullerene derivatives are even more preferred. The term "fullerene derivatives" as used herein means substituted or unsubstituted fullerenes. Any of $C_{60}$, $C_{70}$, $C_{76}$, $C_{78}$, $C_{80}$, $C_{82}$, $C_{84}$, $C_{86}$, $C_{88}$, $C_{90}$, $C_{96}$, $C_{116}$, $C_{180}$, $C_{240}$, and $C_{540}$ is usable as the fullerene, of which substituted or unsubstituted $C_{60}$, $C_{70}$, and $C_{86}$ are preferred and PCBM ([6,6]-phenyl-C61-butyric acid methyl ester) and analogs thereof (the methyl ester whose $C_{60}$ moiety has been substituted with $C_{70}$, $C_{86}$, or the like, the methyl ester whose benzene ring of the substituent has been substituted with another aromatic ring or heterocycle, and the methyl ester whose methyl ester moiety has been substituted with n-butyl ester, i-butyl ester or the like) are even more preferred. The term "phthalocyanines" as used herein means substituted or unsubstituted phthalocyanines and analogs thereof and the term "phthalocyanine analogs" means, in addition to various metal phthalocyanines, tetrapyrazino-porphyrazine, naphthalocyanine, anthracyanine, and the like. As the phthalocyanines, those linked with an electron withdrawing group are preferred, with those substituted with a fluorine atom being more preferred (for example, $F_{16}CuPc$ and FPc-1). Any naphthalenetetracarboxylic acid derivative is usable, but naphthalenetetracarboxylic anhydride (NTCDA), naphthalene bisimide derivative (NTCDI), and perinone pigments (Pigment Orange 43 and Pigment Red 194, and the like) are preferred. The perylenetetracarboxylic acid derivative is not limited, but it is preferably a perylenetetracarboxylic anhydride (PTCDA), perylene bisimide derivative (PTCDI) and a ring-fused product with benzimidazole (PV). Especially preferred examples of the n type organic semiconductor material will next be described.

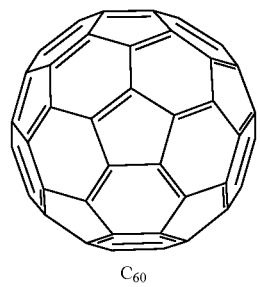

$C_{60}$

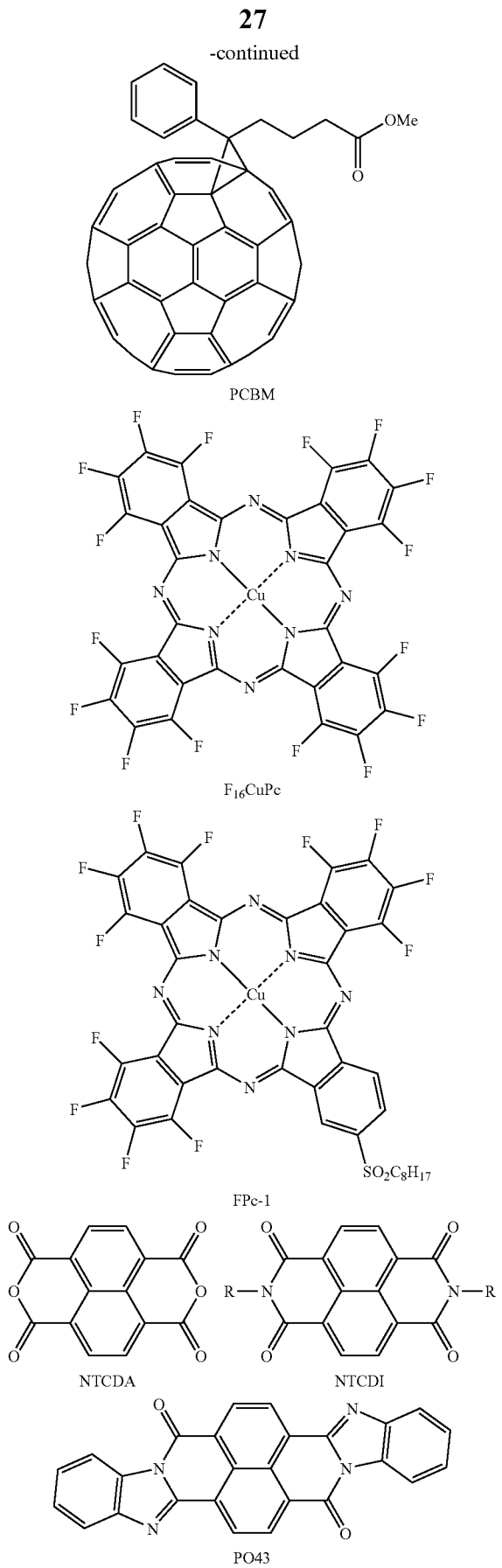

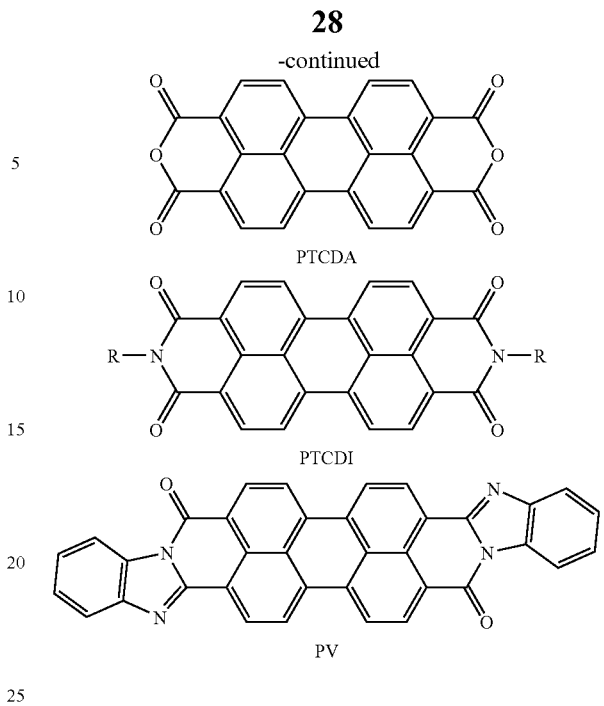

As the material to be used as the buffer layer, any of organic materials and inorganic materials is usable insofar as it has a carrier transport ability. It is preferably an amorphous material. As the buffer material having a hole transport property, any material is usable. It is preferably conductive polymers (for example, PEDOT: PSS), triarylamine derivatives (for example, m-MTDATA), and inorganic semiconductor materials (for example, NiO), with conductive polymers being especially preferred. As the buffer material having an electron transport property, any material is usable. In addition to the materials described above as the n type organic semiconductor material, metal complex compounds (for example, Alq), Bathocuproin, inorganic fluorides (for example, LiF), inorganic oxides (for example, $SiO_x$, $TiO_x$, and ZnO), conductive polymers (for example, cyano-containing polyparaphenylene vinylene (CN-PPV), and perinone polymer (BBL)) are preferred, of which naphthalene derivatives, Bathocuproin, inorganic fluorides, and inorganic oxides are more preferred.

The material to be used as the electrode layer 14 is not particularly limited insofar as it shows conductivity, but materials having high light reflectivity are preferred from the standpoint of enhancing light use efficiency. For example, Al, Pt, W, Au, Ag, Ta, Cu, Cr, Mo, Ti, Ni, Pd, and Zn are preferred, of which Al, Pt, Au, and Ag are more preferred. Although no particular limitation is imposed on the thickness of the electrode layer 14, it is preferably from 1 nm to 1 μm, more preferably from 5 nm to 500 nm.

In order to heighten the storage stability of the element, the element is preferably sealed under an inert atmosphere to keep it in the inert atmosphere. Preferred examples of the sealing material include inorganic materials such as metals, glass, silicon nitride and alumina, and high molecular materials such as parylene. Upon sealing, a desiccant or the like may be sealed together with the element.

The organic thin-film photoelectric conversion element of the invention may be used either for energy conversion (organic thin-film solar cell) or as an optical sensor (solid-state image pickup device, etc.). When the element is used as an optical sensor, it is preferred to apply a bias between the electrode 12 and the electrode 14 and read out a signal in order to improve an S/N ratio. In this case, the bias applied to the photoelectric conversion layer is preferably $1.0 \times 10^5$ V/cm or greater but not greater than $1.0 \times 10^7$ V/cm. A solid-state image pickup device using an organic thin-film photoelectric conversion element is described in detail, for example, in Japanese Patent Laid-Open Nos. 2003-234460, 2003-332551, and 2005-268609 each serving as a reference.

EXAMPLES 1

The invention will hereinafter be described in detail based on some examples. The invention is however not limited to them and various modifications or changes can be made without departing from the scope of the claims.

Compound 1, Compound 12, Compound 26, and Compound 28 were synthesized in accordance with the processes described in *J. Mater. Chem.*, 12, 1671(2002) and *Dyes Pigm.*, 74, 348-356(2007). Compound 8 was synthesized in accordance with the process described in Japanese Patent Laid-Open No. 2000-351774. PCBM was purchased from Frontier Carbon. Comparative Compound P3HT (regioregular, Mw not greater than 87000) was purchased from Sigma-Aldrich. Comparative Compound DCM-1 was synthesized in accordance with the process described in *J. Phys. Chem. C*, 111, 8661(2007).

from the surface of the ITO electrode. A buffer layer having a film thickness of about 50 nm was formed by spin-coating (at 4000 rpm for 60 seconds) a PEDOT (poly(3,4-ethylenedioxythiophene))/PSS (polystyrenesulfonic acid) aqueous solution (Baytron P (standard grade)) onto the ITO substrate and drying at 120° C. for 10 minutes. The film thickness was measured using a stylus profilometer (DEKTAK 6M) (which will be equally applied hereinafter). In a globe box (nitrogen atmosphere), 10 mg of Compound 1 (sample purified by sublimation) and 10 mg of PCBM were dissolved in 1 mL of 1,2-dichlorobenzene (HPLC grade). After the resulting solution was exposed to ultrasonic waves for 5 minutes, the resulting solution was spin coated onto the buffer layer at 1000 rpm to form a photoelectric conversion layer having an almost uniform thickness not greater than 200 nm. A metal electrode was then formed on the photoelectric conversion layer by vacuum deposition of aluminum to give its thickness of 80 nm. In the final step, sealing was performed in the globe box (in a nitrogen atmosphere) while using a sealing can made of glass and a UV curable resin to obtain an organic thin-film photoelectric conversion element having an effective area of $0.04$ $cm^2$.

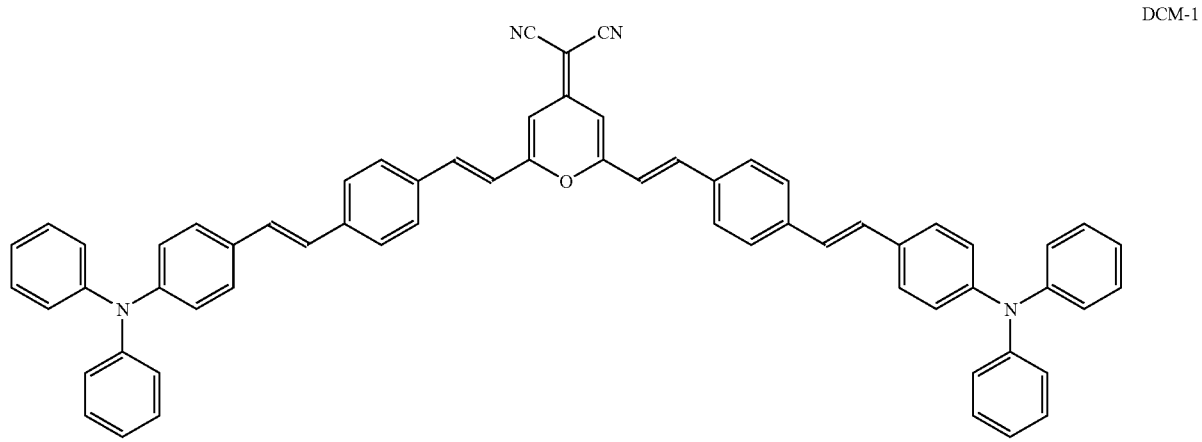

DCM-1

EXAMPLE 1

Compound 1 (molecular weight: 469), Compound 8 (molecular weight: 549), Compound 12 (molecular weight: 496), Compound 26 (molecular weight: 388), and Compound 28 (molecular weight: 694) were purified by sublimation. The results have revealed that appearance of a thermal decomposition product was not observed in any case and they were all purified by sublimation.

COMPARATIVE EXAMPLE 1

Comparative Compound DCM-1 (molecular weight: 887) was purified by sublimation under similar conditions to those employed in Example 1, failing to sublime it without forming a thermal decomposition product.

EXAMPLE 2

Figure 2:
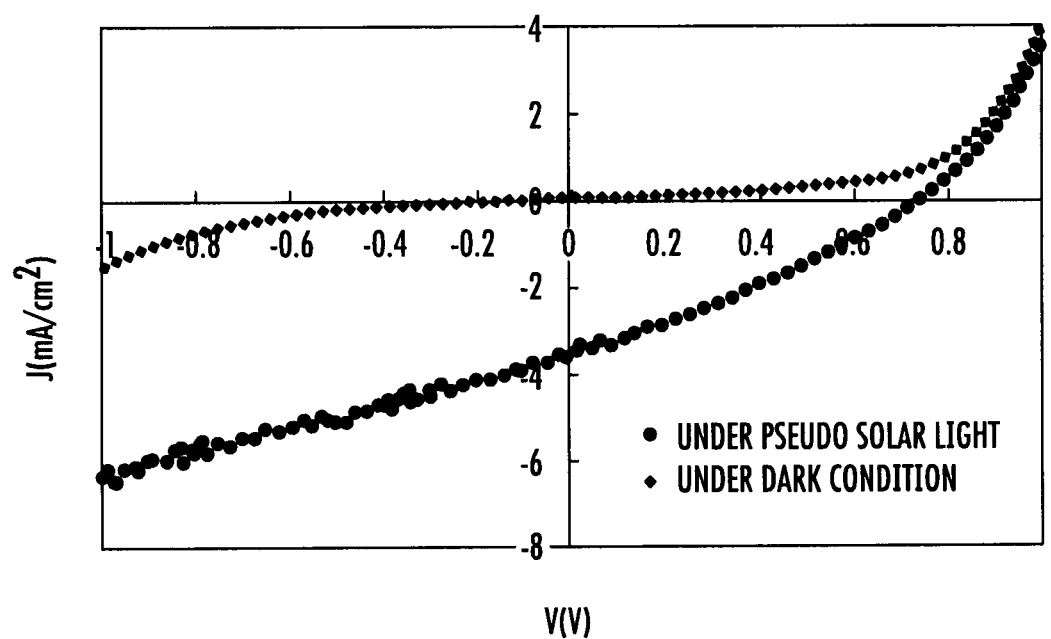
FIG. 2 illustrates current-voltage characteristics of the organic thin-film photoelectric conversion element of the invention using Compound 1 in the dark or under exposure to pseudo solar light (AM 1.5G, 100 mW/cm$^2$).

A glass substrate (2.5 cm×2.5 cm) having a patterned ITO electrode thereon was ultrasonically cleaned in isopropyl alcohol and then dried. It was then subjected to UV ozone treatment for 30 minutes to remove an organic contaminant The resulting element was exposed to pseudo solar light of AM 1.5 and 100 mW/$cm^2$ by using a solar simulator (150 W low-cost type, product of Oriel) and the current-voltage characteristics were measured using an electrochemical analyzer ("ALS Model 660B", product of BAS). As a result, it showed excellent solar cell characteristics as illustrated in FIG. 2. The short-circuit current (Jsc) was 3.6 mA/$cm^2$, open voltage (Voc)=0.74V, and energy conversion efficiency (η) was 0.82%.

Elements produced in a very similar manner except that Compound 8, Compound 12, Compound 26, Compound 28, and the sample of Compound 1 prior to sublimation purification were used instead of Compound 1 also exhibited excellent photoelectric conversion characteristics similar to those of Example 1. Although the sample of Compound 1 prior to sublimation purification also exhibited high photoelectric conversion characteristics, it had a lower photoelectric conversion performance than the sample after sublimation purification. An error at the time of producing the element may lead to an error of about 10% in short-circuit current.

COMPARATIVE EXAMPLE 2

In a very similar manner except that P3HT and DCM-1 were used instead of Compound 1, elements were produced, respectively. The solar cell characteristics of the resulting elements were evaluated under very similar conditions. As shown in Table 1, the resulting elements had a lower photoelectric conversion performance than the elements of the invention.

TABLE 1

| Photoelectric conversion material | Purification by sublimation | Short-circuit current | Open voltage | Remarks |
|---|---|---|---|---|
| Compound 1 | Purified | 3.6 mA/cm² | 0.74 V | Invention |
| Compound 1 | Not purified | 3.1 mA/cm² | 0.71 V | Invention |
| Compound 8 | Purified | 3.2 mA/cm² | 0.70 V | Invention |
| Compound 12 | Purified | 3.4 mA/cm² | 0.72 V | Invention |
| Compound 26 | Purified | 3.0 mA/cm² | 0.67 V | Invention |
| Compound 28 | Purified | 3.3 mA/cm² | 0.73 V | Invention |
| P3HT | Not purrified (impossible) | 3.3 mA/cm² | 0.47 V | Comparative Example |
| DCM-1 | Not purified (impossible) | 1.1 mA/cm² | 0.66 V | Comaprative Example |

As is apparent from the above examples, the organic photoelectric conversion material of the invention permits purification by sublimation. By the purification by sublimation, the organic photoelectric conversion material of the invention can have an improved photoelectric conversion performance so that an element using the material exhibits a high photoelectric conversion performance.

According to the invention, organic photoelectric conversion materials which can be subjected to various chemical modifications and formed into a film by the process of application can be obtained. In addition, organic thin-film photoelectric conversion elements having a high performance, particularly high photoelectric conversion performance, can be obtained by using the organic photoelectric conversion materials.

The entire disclosure of each and every foreign patent application from which the benefit of foreign priority has been claimed in the present application is incorporated herein by reference, as if fully set forth.

What is claimed is:

1. An organic photoelectric conversion material, represented by formula 2 and having a molecular weight of 250 or greater but not greater than 800:

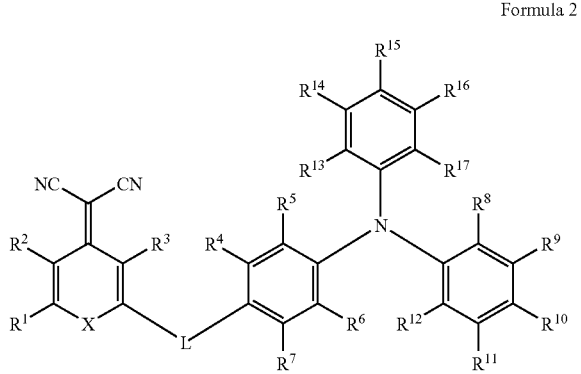

Formula 2 wherein, $R^1$ represents a hydrogen atom, an alkyl group or an aryl group;
$R^2$ to $R^{17}$ each independently represents a hydrogen atom or a substituent;
L represents a divalent π conjugated substituent; and
X represents O, S, or N—$R^a$ in which $R^a$ represents a hydrogen atom or a substituent.

2. The organic photoelectric conversion material according to claim 1, which has a molecular weight of 300 or greater but not greater than 800.

3. The organic photoelectric conversion material according to claim 1, which has a molecular weight of 400 or greater but not greater than 800.

4. A photoelectric conversion element, comprising:
two electrode layers; and
a photoelectric conversion layer located between the two electrode layers,
wherein the photoelectric conversion layer contains a blend film containing an organic photoelectric conversion material and an n type organic semiconductor material, said organic photoelectric conversion material being represented by formula 2 and having a molecular weight of 250 or greater but not greater than 800:

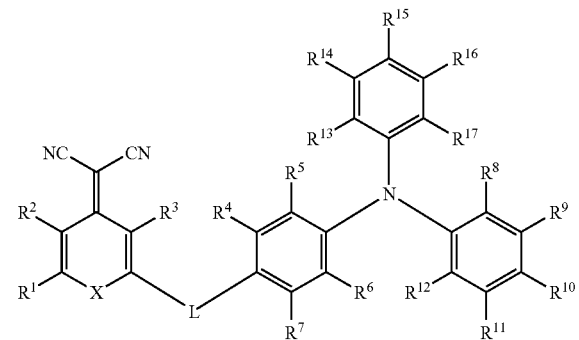

Formula 2 wherein, $R^1$ represents a hydrogen atom, an alkyl group or an aryl group;
$R^2$ to $R^{17}$ each independently represents a hydrogen atom or a substituent;
L represents a divalent π conjugated substituent; and
X represents O, S, or N—$R^a$ in which $R^a$ represents a hydrogen atom or a substituent.

5. The photoelectric conversion element according to claim 4, wherein the n type organic semiconductor material is at least one selected from the group consisting of fullerene derivatives, phthalocyanines, naphthalenetetracarboxylic acid derivatives, and perylenetetracarboxylic acid derivatives.

6. The photoelectric conversion element according to claim 4, wherein the n type organic semiconductor material is a fullerene derivative.

7. The photoelectric conversion element according to claim 4, wherein the photoelectric conversion layer is formed by a solution application process.

8. The photoelectric conversion element according to claim 7, wherein a solvent used in the solution application process includes at least one solvent having a boiling point of 135° C. or greater but less than 300° C.

9. The photoelectric conversion element according to claim 4, further comprising:
a buffer layer having a conductive polymer, the buffer layer located between one of the two electrode layers and the photoelectric conversion layer.

10. The photoelectric conversion element according to claim 4, which is sealed in an inert atmosphere after formation of the photoelectric conversion element.

11. The photoelectric conversion element according to claim 4,
wherein the photoelectric conversion layer has a thickness of from 1 nm to 1 µm.

12. The organic photoelectric conversion material according to claim 1, wherein $R^1$ is a hydrogen atom, a t-butyl group or an unsubstituted aryl group.

13. The photoelectric conversion element according to claim 4, wherein $R^1$ is a hydrogen atom, a t-butyl group or an unsubstituted aryl group.

* * * * *